C. W. REITLER.
Assignor of one-fourth to W. T. JENISON.
ELECTRIC PEN HOLDER.
No. 11,053. Reissued Jan. 7, 1890.
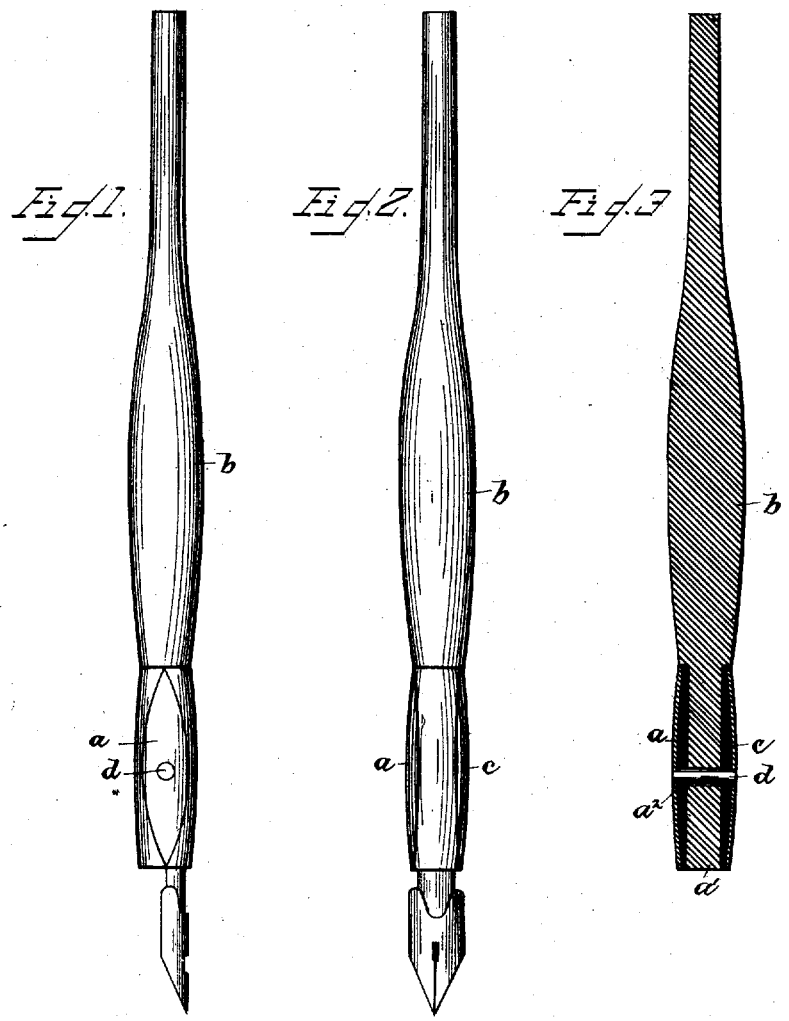
Witnesses.
Wm. S. Hodges.
C. C. Shaw
Inventor.
Charles W. Reitler,
By
Attorney.
N. PETERS, Photo-Lithographer, Washington, D. C.

UNITED STATES PATENT OFFICE.

CHARLES W. REITLER, OF DENVER, COLORADO, ASSIGNOR OF ONE-FOURTH TO WILLIAM T. JENISON, OF SAME PLACE.

ELECTRIC PEN-HOLDER.

SPECIFICATION forming part of Reissued Letters Patent No. 11,053, dated January 7, 1890.

Original No. 381,953, dated May 1, 1888. Application for reissue filed September 23, 1889. Serial No. 324,832.

*To all whom it may concern:*

Be it known that I, CHARLES W. REITLER, a citizen of the United States, residing at Denver, in the county of Arapahoe and State of Colorado, have invented certain new and useful Improvements in Electric Pen-Holders; and I do hereby declare the following to be a full, clear, and exact description of the invention, such as will enable others skilled in the art to which it appertains to make and use the same, reference being had to the accompanying drawings, and to the letters of reference marked thereon, which form a part of this specification.

This invention relates to a pen-holder having a therapeutic electric attachment for generating an electric current to pass through the fingers of the operator.

The object of my invention is to provide an improved pen-holder with electrodes or plates, forming a voltaic pile or galvanic battery by which a current of electricity may be generated by the action of the salts exuding from the fingers of the writer while the holder is being used, whereby an electric current may be passed through the fingers of the writer, thus preventing and also curing "scriveners' palsy" or "writers' cramp," and at the same time strengthen the nerves of the fingers coming in contact with the same.

With these and other objects in view my invention consists of a therapeutic pen-holder having a tenon end and opposite electrodes or plates embedded in suitable insulating material and connected together by a rivet or pin, which fits in the opening of said tenon end of the holder, substantially as hereinafter fully set forth, and particularly pointed out in the claims.

In the accompanying drawings, Figures 1 and 2 are views in side elevation of my improved pen-holder, said views being taken at right angles to each other. Fig. 3 is a longitudinal sectional view.

Referring to the drawings, *b* designates the shaft of the pen-holder, the same being provided with a tenon end $a'$, wherein is formed a hole or opening $a^2$, as shown in Fig. 3. Around or upon this tenon end I apply an insulating material—such as rubber, gutta-percha, celluloid, or any suitable equivalent of either or all of them. On opposite sides of this insulating material, which is in the form of a sleeve, I place plates or electrodes *a* and *c*, of opposite polarity, one being of copper and the other of zinc. These plates are secured together by a rivet or cross-pin *d*, of copper, passed through the opening referred to. By this construction an electric current is made to pass through the entire lengths of the fingers, or a finger and thumb of the operator, thus deriving the greatest possible therapeutic benefit from the use of the current, and thus preventing and curing scriveners' palsy or writers' cramp, and imparting strength and firmness to the hand and fingers of the operator. Thus a maximum amount of work may be accomplished without tiring or cramping the hand of the operator, who is enabled thereby to do continuous work of a superior order.

While I have shown and described the tenon end of the holder as provided with a hole for the reception of the rivet, it is obvious that any opening in the said end that provides for the reception of the rivet is within the scope of my invention, and hence the latter can be modified to such an extent as to provide for the passage of the rivet.

I claim as my invention—

1. The herein-described therapeutic pen-holder, consisting of a shaft having the electrodes or plates arranged and secured on opposite sides thereof, and an insulating material interposed between the plates and the pen-holder, as set forth.

2. The herein-described improved therapeutic pen-holder, consisting of a shaft having a lower tenon end provided with an opening therein, the electrodes or plates arranged and secured on opposite sides of said end, the insulating material interposed between the plates and pen-holder, and the rivet or pin connecting said plates, substantially as set forth.

In testimony whereof I affix my signature in presence of two witnesses.

CHARLES W. REITLER.

Witnesses:
D. STREET,
ROBT. E. FOOT.